United States Patent [19]

Noble

[11] Patent Number: 5,506,368

[45] Date of Patent: *Apr. 9, 1996

[54] INBRED CORN LINE PHN82

[75] Inventor: Stephen W. Noble, Johnston, Iowa

[73] Assignee: Pioneer Hi-Bred International, Inc., Des Moines, Iowa

[*] Notice: The term of this patent shall not extend beyond the expiration date of Pat. No. 5,157,206.

[21] Appl. No.: 305,500

[22] Filed: Sep. 13, 1994

Related U.S. Application Data

[60] Continuation-in-part of Ser. No. 860,666, Mar. 30, 1992, abandoned, which is a division of Ser. No. 402,010, Aug. 30, 1989, Pat. No. 5,157,206.

[51] Int. Cl.$^6$ .............................. A01H 5/00; A01H 4/00; A01H 1/00; C12N 5/04
[52] U.S. Cl. .................. 800/200; 800/250; 800/DIG. 56; 435/240.4; 435/240.49; 435/240.5; 47/58
[58] Field of Search ..................................... 800/200, 205, 800/DIG. 56, 250; 47/58.03, 58.05; 435/240.4, 240.45, 240.49, 240.50

[56] References Cited

U.S. PATENT DOCUMENTS 4,594,810  6/1986  Troger ........................................ 47/58

OTHER PUBLICATIONS

Poehlman (1987) Breeding Field Crops. AVI Publishers Co. pp. 237–247.
Meglyi et al. (1984) Crop Science vol. 24. pp. 545–549.

Primary Examiner—Gary Benzion
Attorney, Agent, or Firm—Pioneer Hi-Bred International, Inc.

[57] ABSTRACT

According to the invention, there is provided an inbred corn line, designated PHN82. This invention thus relates to the plants and seeds of inbred corn line PHN82 and to methods for producing a corn plant produced by crossing the inbred line PHN82 with itself or with another corn plant. This invention further relates to hybrid corn seeds and plants produced by crossing the inbred line PHN82 with another corn line or plant and to crosses with related species.

3 Claims, No Drawings

5,506,368

1

INBRED CORN LINE PHN82

CROSS REFERENCE TO RELATED APPLICATION

This is a continuation in part of prior copending application Ser. No. 07/860,666 filed Mar. 30, 1992, now abandoned, which was a division of application Ser. No. 07/402,010, Aug. 30, 1989, now U.S. Pat. No. 5,157,206.

FIELD OF THE INVENTION

This invention is in the field of corn breeding, specifically relating to an inbred corn line designated PHN82.

BACKGROUND OF THE INVENTION

The goal of plant breeding is to combine in a single variety/hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci. A cross of two plants each heterozygous at a number of gene loci will produce a population of hybrid plants that differ genetically and will not be uniform.

Corn plants (*Zea mays* L.) can be bred by both self-pollination and cross-pollination techniques. Corn has separate male and female flowers on the same plant located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding for single-gene traits starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred lines, each of which has a genotype which complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, each breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)× (C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop high-yielding corn hybrids that are agronomically sound based on stable inbred lines. The reasons for this goal are obvious: to maximize the amount of grain produced with the inputs used and minimize susceptibility to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

SUMMARY OF THE INVENTION

According to the invention, there is provided a novel inbred corn line, designated PHN82. This invention thus relates to the seeds of inbred corn line PHN82, to the plants of inbred corn line PHN82, and to methods for producing a corn plant produced by crossing the inbred line PHN82 with itself or another corn line. This invention further relates to hybrid corn seeds and plants produced by crossing the inbred line PHN82 with another corn line or a related species.

DEFINITIONS

In the description and examples that follow, a number of terms are used herein. In order to provide a clear and consistent understanding of the specification and claims, including the scope to be given such terms, the following definitions are provided:

BAR PLT=BARREN PLANTS. This is the number of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest adjusted to 15.5% moisture. ABS is in absolute terms and % MN is percent of the mean for the experiments in which the inbred or hybrid was grown.

CLD TST=COLD TEST. This is the percentage of kernels that germinate under cold soil conditions. ABS=absolute measurement and % MN is percentage of mean of the experiments in which inbred or hybrid was grown.

COB SC=COB SCORE. The cob score is a rating of how well the grain is shelled off the cob and how badly the cob is broken up going through the combine. This is given as a 1 to 9 score with 9 being very good. A high score indicates that the grain shells off of the cob well, and the cob does not break.

DRP EAR=DROPPED EARS. This is a measure of the number of dropped ears per plot and represents the percentage of plants that did not drop ears prior to harvest.

EAR HT=EAR HEIGHT. The ear height is a measure from the ground to the top developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN QUL=GRAIN QUALITY. This is a 1 to 9 rating for the general quality of the shelled grain as it is harvested based on such factors as the color of the harvested grain, any mold on the grain, and any cracked grain. High scores indicate good grain quality.

KER LB=KERNELS PER POUND. This is the number of kernels per 0.1 pound.

KSZ L=KERNEL SIZE LARGE. Percentage by weight of shelled corn that passes through a screen with 25/64 inch diameter openings but does not pass through a screen with 22/64 inch diameter openings.

KSZ MF=KERNEL SIZE MEDIUM FLAT. Percentage by weight of shelled corn that passes through a screen with 22/64 inch diameter openings and a screen with 13/64 inch wide slot screen but does not pass through a screen with 18.5/64 inch diameter openings.

KSZ MR=KERNEL SIZE MEDIUM ROUND. Percentage by weight of shelled corn that passes through a screen with 22/64 inch diameter openings but does not pass through a 13/64 inch wide slot screen or a screen with 18.5/64 inch diameter openings.

KSZ S=KERNEL SIZE SMALL. Percentage by weight of shelled corn that passes through a screen with 18.5/64 inch diameter openings but does not pass through a screen with 16/64 inch diameter openings.

KSZ TIP=KERNEL SIZE TIPS. Percentage by weight of shelled corn that passes through a screen with 16/64 inch diameter openings.

KSZ XL=KERNEL SIZE EXTRA LARGE. Percentage by weight of shelled corn that does not pass through a screen with 25/64 inch diameter openings.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL WT=POLLEN WEIGHT. This is the weight of pollen per 100 plants taken on a plot basis. ABS refers to data in absolute, and % MN refers to data presented as percentage, of experimental mean.

PRM=PREDICTED RM. This trait, predicted relative maturity (RM), is based on the harvest moisture of the grain. The relative maturity rating is based on a known set of checks and utilizes standard linear regression analyses and is referred to as the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT UNADJUSTED. The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

CLN=Corn Lethal Necrosis (MCMV=Maize Chlorotic Mottle Virus and MDMV=Maize Dwarf Mosaic Virus): Visual rating (1–9 score) where a "1" is very susceptible and a "9" is very resistant.

MDM CPX=Maize Dwarf Mosaic Complex (MDMV= Maize Dwarf Mosaic Virus & MCDV=Maize Chlorotic Dwarf Virus): Visual rating (1–9 score) where a "1" is very susceptible and a "9" is very resistant.

COM SMT=Common Smut (*Ustilago maydis*): Percentage of plants that did not have infection.

ANT ROT=Anthracnose Stalk Rot (*Colletotrichum graminicola*): Visual rating (1–9 score) where a "1" is very susceptible and a "9" is very resistant.

SLF BLT=Southern Leaf Blight (*Bipolaris maydis, Helminthosporium maydis*): Visual rating (1–9 score) where a "1" is very susceptible and a "9" is very resistant.

NLF BLT=Northern Leaf Blight (*Exserohilum turcicum, H. turcicum*): Visual rating (1–9 score) where a "1" is very susceptible and a "9" is very resistant.

HC BLT=Helminthosporium Carbonum Leaf Blight (Bipolariszeicola, *H. carbonum*): Visual rating (1–9 score) where a "1" is very susceptible and a "9" is very resistant.

COM RST=Common Rust (*Puccinia sorghi*): Visual rating (1–9 score) where a "1" is very susceptible and a "9" is very resistant.

SO RST=Southern Rust (*Puccinia polysora*): Visual rating (1–9 score) where a "1" is very susceptible and a "9" is very resistant.

EYE SPT=Eyespot (*Kabatiella zeae*): Visual rating (1–9 score) where a "1" is very susceptible and a "9" is very resistant.

GLF SPT=Gray Leaf Spoil (*Cercospora zeae-maydis*): Visual rating (1–9 score) where a "1" is very susceptible and a "9" is very resistant.

STW WLT=Stewart's Wilt (*Erwinia stewartii*): Visual rating (1–9 score) where a "1" is very susceptible and a "9" is very resistant.

GOS WLT=Goss's Wilt (*Corynebacterium nebraskense*): Visual rating (1–9 score) where a "1" is very susceptible and a "9" is very resistant.

HD SMT=Head Smut (*Spacelotheca reiliana*): Percentage of plants that did not have infection.

DNY MIL=Downy Mildew (*Peronosclerospora sorghi*): Percentage of plants that did not have infection.

FUS EAR=Fusarium Ear Mold (*Fusarium moniliforme*): Percentage of plants that did not have infection.

EAR MLD=General Ear Mold: Visual rating (1–9 score) where a "1" is very susceptible and a "9" is very resistant. This is based on overall rating for ear mold of mature ears without determining specific mold organism, and may not be predictive for a specific ear mold. ECB DPE=Dropped ears due to European Corn Borer (*Ostrinia nubilalis*): Percentage of plants that did not drop ears under second brood corn borer infestation. ECB 2SC=European Corn Borer Second Brood (Ostrinia nubilalis): Visual rating (1–9 score) of post flowering damage due to infestation by European Corn Borer. A "1" is very susceptible and a "9" is very resistant. ECB 1LF=European Corn Borer First Brood (*Ostrinia nubilalis*): Visual rating (1–9 score) of pre-flowering leaf feeding by European Corn Borer. A "1" is very susceptible and a "9" is very resistant.

ECB 2IT=European Corn Borer Second Brood Tunneling (*Ostrinia nubilalis*): The average inches of tunneling in the stalk due to second brood (post-flowering) European Corn Borer infestation. Determined by splitting stalks with a knife, from four internodes above the ear to the ground.

DETAILED DESCRIPTION OF THE INVENTION

Inbred Corn Line PHN82 is a yellow, dent corn inbred with superior characteristics and provides a very good female parental line in crosses for producing first generation $F_1$ corn hybrids. This inbred is adapted across most regions of the United States. The inbred can be used to produce hybrids from approximately 116–128 relative maturity based on the Minnesota Relative Maturity Rating System for harvest moisture of grain. PHN82's high yielding ability combined with good drought tolerance and distribution of kernel size make it most useful as a female parent. It can be used as a male parent but it is marginal because of its light pollen yield. The inbred was 84% of the experimental mean for amount of pollen in the pollen yield test over 13 locations.

The inbred has shown uniformity and stability within the limits of environmental influence for all the traits as described in the Variety Description Information (Table 1) that follows. Most of the data in the Variety Description information was collected at Johnston, Iowa. The inbred has been self-pollinated and ear-rowed a sufficient number of generations with careful attention paid to uniformity of plant type to ensure homozygosity and phenotypic stability. The line has been increased both by hand and in isolated fields with continued observation for uniformity. No variant traits have been observed or are expected in PHN82.

Inbred corn line PHN82, being substantially homozygous, can be reproduced by planting seeds of the line, growing the resulting corn plants under self-pollinating or sib-pollinating conditions with adequate isolation, and harvesting the resulting seed, using techniques familiar to the agricultural arts.

TABLE 1

PHN82
VARIETY DESCRIPTION INFORMATION

Type: Dent      Region Best Adapted: Most Regions
A. Maturity: Averaged across maturity zones. Zone: 0

INBRED = PHN82
| | |
|---|---|
| Heat Unit Shed: | 1460 |
| Heat Unit Silk: | 1500 |
| No. Reps: | 82 |

$$\text{HEAT UNITS} = \frac{[\text{Max. Temp.} (\leq 86° \text{ F.}) + \text{Min. Temp} (\geq 50° \text{ F.})]^*}{2} - 50$$

B. Plant Characteristics:

| | |
|---|---|
| Plant height (to tassel tip): | 209 cm |
| Length of top ear internode: | 13 cm |
| Number of ears per stalk: | single ear |
| Ear height (to base of top ear): | 81 cm |
| Number of tillers: | None |
| Cytoplasm type: | Normal |

C. Leaf:

| | |
|---|---|
| Color: | (WF9) Medium green |
| Angle from Stalk: | 30–60 degrees |
| Marginal waves: | (OH7L) Many |
| Number of Leaves (mature plants): | 18 |
| Sheath Pubescence: | (W22) Light |
| Longitudinal Creases: | (PA11) Many |
| Length (Ear node leaf): | 79 cm |
| Width (widest point, ear node leaf): | 9 cm |

D. Tassel:

| | |
|---|---|
| Number lateral branches: | 6 |
| Branch Angle from central spike: | >45 degrees |
| Pollen Shed: | Light based on Pollen Yield Test (84% of experiment mean). |
| Peduncle Length (top leaf to basal branches): | 18 cm |
| Anther Color: | Reddish-purple |
| Glume Color: | Green |

E. Ear (Husked Ear Data Except When Stated Otherwise):

| | |
|---|---|
| Length: | 17 cm |
| Weight: | 132 gm |
| Mid-point Diameter: | 41 mm |
| Silk Color: | Pink |
| Husk Extension (Harvest stage): | Medium (barely covering ear) |
| Husk Leaf: | Long (>15 cm) |
| Taper of Ear: | Slight taper |
| Position of shank (dry husks): | Upright |
| Kernel Rows: | Distinct, Straight, Number = 16 |
| Husk Color (fresh): | Light green |
| Husk Color (dry): | Buff |
| Shank Length: | 11 cm |
| Shank (No. of internodes): | 8 |

F. Kernel (Dried):

Size (from ear mid-point)
| | |
|---|---|
| Length: | 11 mm |
| Width: | 8 mm |

TABLE 1-continued

PHN82
VARIETY DESCRIPTION INFORMATION

| | |
|---|---|
| Thick: | 5 mm |
| Shape Grade (% rounds): | 20–40% medium rounds based on Parent Test Data |
| Pericarp Color: | Colorless |
| Aleurone Color: | Homozygous yellow |
| Endosperm Color: | Yellow |
| Endosperm Type: | Normal |
| Gm Wt/100 Seeds (unsized): | 26 gm |
| G. Cob: | |
| Diameter at mid-point: | 27 mm |
| Strength: | Strong |
| Color: | Pinkish-red |
| H. Diseases: | |
| Corn Lethal Necrosis (MCMV = Maize Chlorotic Mottle Virus and MDMV = Maize Dwarf Mosaic Virus): | Susceptible |
| Maize Dwarf Mosaic Complex (MDMV & MCDV = Maize Chlorotic Dwarf Virus): | Susceptible |
| Anthracnose Stalk Rot (*C. Graminicola*): | Intermediate |
| S. Leaf Blight (*H. Maydis*): | Intermediate |
| N. Leaf Blight (*H. Urcicum*): | Intermediate |
| Carbonum Leaf Blight (*H. Carbonum*): | Intermediate |
| Common Rust (*P. Sorghi*): | Intermediate |
| Eye Spot (*K. Zeae*): | Susceptible |
| Gray Leaf Spot (*C. Zeae*): | Susceptible |
| Stewarts Wilt (*E. Stewartii*): | Resistant |
| Goss's Wilt (*C. Nebraskense*): | Resistant |
| Common Smut (*U. Maydis*): | Resistant |
| Head Smut (*S. Reiliana*): | Intermediate |
| Downy Mildew (*S. Sorghi*): | Resistant |
| Fusarium Ear Mold (*F. Moniliforme*): | Susceptible |
| I. Insects: | |
| European Corn Borer-1 Leaf Damage (Preflowering): | Intermediate |
| European Corn Borer-2 (Post-flowering): | Intermediate |
| J. Variety Most Closely Resembling: | |
| Character | Inbred |
| Maturity | PHV78 |
| Usage | PHV78 |

*If maximum is greater than 86 degrees fahrenheit, then 86 is used and if minimum is less than 50, then 50 is used. Heat units accumulated daily and can not be less than 0.

PHV78 (PVP Certificate No. 8800003 and U.S. Pat. No. 4,812,599) is a Pioneer Hi-Bred International, Inc. proprietary inbred.

Data for items B, C, D, E, F, and G is based primarily on a maximum of three reps of data from Johnston, Iowa grown in 1987 and 1988, plus description information from the maintaining station.

TABLE 2

ELECTROPHORESIS RESULTS
Isozyme Genotypes for PHN82
Alleles Present

| Loci | PHN82 |
|---|---|
| ACP1 | 2 |
| ADH1 | 4 |
| CAT3 | 9 |
| DIA1 | 8 |
| GOT1 | 4 |
| GOT2 | 4 |
| GOT3 | 4 |
| IDH1 | 4 |
| IDH2 | 6 |
| MDH1 | 6 |
| MDH2 | 3.5 |
| MDH3 | 16 |
| MDH4 | 12 |
| MDH5 | 12 |
| MMM | 4 |
| PGM1 | 9 |
| PGM2 | 3 |
| PGD1 | 3.8 |
| PGD2 | 5 |
| PHI1 | 4 |

Isozyme data was generated for inbred corn line PHN82 according to the procedure described in Goodman, M. M. and Stuber, C. M., "Genetic identification of lines and crosses using isoenzyme electrophoresis," Proceedings of the Thirty-Fifth Annual Corn and Sorghum Industry Research Conference, Chicago, Illinois (1980).

INDUSTRIAL APPLICABILITY

This invention also is directed to methods for producing a corn plant by crossing a first parent corn plant with a second parent corn plant wherein the first or second parent corn plant is an inbred corn plant from the line PHN82.

Further, both first and second parent corn plants can come from the inbred corn line PHN82. Thus, any such methods using the inbred corn line PHN82 are part of this invention: selfing, backcrosses, hybrid production, crosses to populations, and the like. All plants produced using inbred corn line PHN82 as a parent are within the scope of this invention. Advantageously, the inbred corn line is used in crosses with other, different, corn inbreds to produce first generation ($F_1$) corn hybrid seeds and plants with superior characteristics.

As used herein, the terms "plant and plant parts" include plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottsville, Va. 1982, at 367–372. Thus, another aspect of this invention is to provide cells which upon growth and differentiation produce the inbred line PHN82.

The utility of inbred line PHN82 also extends to crosses with other species. Commonly, suitable species will be of the family Graminaceae, and especially of the genera Zea, Tripsacum, Coix, Schlerachne, Polytoca, Chionachne, and Trilobachne, of the tribe Maydeae. Of these, Zea and Tripsacum, are most preferred. Potentially suitable for crosses with PHN82 may be the various varieties of grain sorghum, *Sorghum bicolor* (L.) Moench.

Corn is used as human food, livestock feed, and as raw material in industry. The food uses of corn, in addition to human consumption of corn kernels, include both products of dry- and wet-milling industries and alkaline cooking. The principal products of corn dry milling are grits, meal and flour. The corn wet-milling industry can provide corn starch, corn syrups, and dextrose for food use. Alkaline cooking provides snack foods (i.e., corn chips, tortillas, etc.) Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHN82, the plant produced from the inbred seed, the hybrid corn plant produced from the crossing of the inbred, hybrid seed, and various parts of the hybrid corn plant can be utilized for human food, livestock feed, and as a raw material in industry.

EXAMPLE

INBRED AND HYBRID PERFORMANCE OF PHN82

In the examples that follow the traits and characteristics of inbred corn line PHN82 are given as a line and in hybrid combination. The data collected on inbred corn line PHN82 is presented for the key characteristics and traits.

The results in Table 3 compare PHN82 to PHV78. PHV78 (PVP Certificate #8800003, U.S. Pat. No. 4,812,599) is an important inbred that would be used in the area that PHN82 would be used and would cross well with some of the same inbred lines. The results of data collected over four years of research testing show that the two lines differ significantly for a number of traits. PHN82 offers some key advantages over PHV78 in that it had an 11.6 percent higher yield than PHV78, fewer barren plants, better early stand establishment, better grain quality with higher test weight and fewer brittle stalks. PHN82 is earlier flowering and is a somewhat shorter plant than PHV78. In the areas of resistance to disease and insects, PHN82 had greater resistance to common rust and was more resistant to ear mold than PHN82. Both PHN82 and PHV78 can be used as males in the production of corn hybrids but PHN82 also makes a very good female while PHV78 is not an acceptable female.

The results in Table 4 compare PHN82 to PHV78 crossed to the same inbred testers. The results also show that the two lines differ significantly for a number of traits in hybrid combination. PHN82 offers some key advantages over PHV78 in hybrid combination for stalk lodging, root lodging, stay green and grain quality. The PHN82 hybrids were somewhat earlier maturing than the PHV78 hybrids for harvest moisture of the grain and flowering. PHN82 hybrids are shorter and lower eared than PHV78 hybrids which is important to grain farmers. PHN82 hybrids generally have better drought tolerance than PHV78 hybrids based on results under stress conditions.

The results in Table 5 compare a PHN82 hybrid to Pioneer® brand 3379. These hybrids have a parent in common that is not PHN82. Pioneer® brand 3379 is a very important hybrid grown in the same area as the PHN82 hybrid. The PHN82 hybrid has some important advantages over 3379. Although it yielded 1% less it was 0.7 of a point drier for grain harvest moisture, shed pollen earlier, is shorter and lower eared than 3379. The PHN82 hybrid also reaches black layer earlier than 3379 and will be utilized farther north than 3379 as well as in some of the same areas as 3379. In 1988 farmer grown strip tests for 263 side by side comparisons, the PHN82 hybrid yielded 1.6 bushels per acre more than 3379 and was 1.0% drier for harvest grain moisture.

PAIRED INBRED COMPARISON DATA
INBRED #1 - PHN82
INBRED #2 - PHV78

| YEAR | VAR # | BU ACR ABS | BU ACR % MN | BAR PLT ABS | BRT STK ABS | EAR HT ABS | EAR SZ ABS | EST CNT ABS | CLD TST ABS | CLD TST % MN | DRP EAR ABS | TIL LER ABS | GDU SHD ABS | GDU SLK ABS |
|---|---|---|---|---|---|---|---|---|---|---|---|---|---|---|
| TOTAL SUM | 1 | 93.4 | 126 | 93.3 | 97.5 | 27.0 | 6.3 | 33.5 | 88.3 | 101 | 100.0 | 1.0 | 145.3 | 151.5 |
| | 2 | 81.8 | 108 | 90.7 | 93.9 | 31.9 | 7.1 | 31.3 | 87.0 | 99 | 99.9 | 1.5 | 157.8 | 164.1 |
| | LOCS | 17 | 17 | 18 | 8 | 30 | 22 | 92 | 3 | 3 | 6 | 32 | 90 | 84 |
| | DIFF | 11.6 | 18 | 2.6 | 3.6 | 5.0 | 0.8 | 2.1 | 1.3 | 2 | 0.1 | 0.5 | 12.5 | 12.6 |
| | PROB | .011+ | .023+ | .002# | .205 | .000# | .000# | .000# | .794 | .788 | .363 | .394 | .000# | .000# |

| YEAR | VAR # | GRN QUL ABS | KER LB ABS | KSZ XL ABS | KSZ L ABS | KSZ MR ABS | KSZ MF ABS | KSZ S ABS | KSZ TIP ABS | MST ABS | PLT HT ABS | POL WT ABS | POL WT % MN | POL SC ABS | RT LDG ABS |
|---|---|---|---|---|---|---|---|---|---|---|---|---|---|---|---|
| TOTAL SUM | 1 | 7.2 | 39.5 | 1.0 | 30.0 | 22.3 | 34.7 | 10.7 | 1.3 | 21.2 | 71.9 | 164.7 | 91 | 5.2 | 84.4 |
| | 2 | 6.4 | 37.8 | 8.7 | 53.7 | 16.7 | 16.3 | 3.7 | 1.0 | 18.9 | 87.3 | 254.2 | 137 | 6.7 | 86.4 |
| | LOCS | 13 | 3 | 3 | 3 | 3 | 3 | 3 | 3 | 17 | 31 | 6 | 6 | 46 | 8 |
| | DIFF | 0.9 | 1.6 | 7.7 | 23.7 | 5.7 | 18.3 | 7.0 | 0.3 | 2.3 | 15.4 | 89.4 | 46 | 1.5 | 2.0 |
| | PROB | .098* | .340 | .208 | .019+ | .142 | .014+ | .026+ | .423 | .000# | .000# | .158 | .170 | .000# | .481 |

| YEAR | VAR # | TAS BLS ABS | TAS SZ ABS | TAS WT ABS | TEX EAR ABS | TST WT ABS | SCT GRN ABS | SDG VGR ABS | STA GRN ABS | STK CNT ABS | STK LDG ABS | YLD SC ABS | COM RST ABS |
|---|---|---|---|---|---|---|---|---|---|---|---|---|---|
| TOTAL SUM | 1 | 8.7 | 4.6 | 3.4 | 5.6 | 56.0 | 6.8 | 5.0 | 6.2 | 29.7 | 97.4 | 6.5 | 5.0 |
| | 2 | 9.0 | 7.2 | 7.2 | 4.3 | 54.3 | 5.5 | 5.2 | 5.6 | 28.9 | 95.3 | 6.1 | 2.5 |
| | LOCS | 3 | 36 | 6 | 18 | 14 | 31 | 52 | 33 | 80 | 9 | 36 | 2 |
| | DIFF | 0.3 | 2.6 | 3.8 | 1.3 | 1.7 | 1.3 | 0.2 | 0.6 | 0.8 | 2.1 | 0.4 | 2.5 |
| | PROB | .423 | .000# | .001# | .000# | .000# | .000# | .229 | .037+ | .026+ | .269 | .096* | .126 |

| YEAR | VAR # | COM SMT ABS | EAR MLD ABS | ECB DPE ABS | ECB 1LF ABS | ECB 2SC ABS | EYE SPT ABS | FUS EAR ABS | GLF SPT ABS | HC BLT ABS | MDM CPX ABS | NLF BLT ABS | SLF BLT ABS | SO RST ABS | STW WLT ABS |
|---|---|---|---|---|---|---|---|---|---|---|---|---|---|---|---|
| TOTAL SUM | 1 | 0.0 | 6.5 | 76.7 | 4.9 | 4.3 | 3.0 | 31.5 | 2.2 | 5.0 | 2.5 | 5.3 | 4.8 | 6.0 | 7.5 |
| | 2 | 1.0 | 5.1 | 73.3 | 6.1 | 4.7 | 3.0 | 12.8 | 3.1 | 6.0 | 3.0 | 5.9 | 4.8 | 6.0 | 7.5 |
| | LOCS | 1 | 30 | 1 | 24 | 6 | 1 | 2 | 5 | 1 | 1 | 4 | 3 | 1 | 2 |
| | DIFF | 1.0 | 1.4 | 3.3 | 1.2 | 0.4 | 0.0 | 18.8 | 0.9 | 1.0 | 0.5 | 0.6 | 0.0 | 0.0 | 0.0 |
| | PROB | | .000# | | .002# | .658 | | .500 | .088* | | | .464 | .000# | | 1.00 |

* = 10% SIG
+ = 5% SIG
# = 1% SIG

Average Inbred by Tester Performance Comparing PHN82 to PHV78
crossed to the same Inbred Testers and Grown in the Same Experiments.
All Values are Expressed as percent of the experiment mean
except Predicted RM, Selection Index, and Yield (Bu./Ac.).

| | Inbred | PRM | SEL IND | BU ACR | YLD | MST | GDU SHD | STK LDG | RT LDG | BAR PLT |
|---|---|---|---|---|---|---|---|---|---|---|
| TOTAL | REPLIC. | 553 | 569 | 569 | 569 | 579 | 161 | 527 | 270 | 186 |
| MEAN WTS | PHN82 | 120 | 103 | 139 | 103 | 100 | 98 | 101 | 101 | 102 |
| MEAN WTS | PHV78 | 122 | 103 | 142 | 104 | 103 | 102 | 99 | 98 | 99 |
| | DIFF | 2 | | 3 | 1 | 2 | 4 | 2 | 3 | 3 |

| | Inbred | STA GRN | TST WTA | COB SC | GRN QUL | SDG VGR | EST CNT | PLT HT | EAR HT | DRP EAR | BRT STK |
|---|---|---|---|---|---|---|---|---|---|---|---|
| TOTAL | REPLIC. | 412 | 577 | 29 | 103 | 238 | 298 | 297 | 299 | 335 | 10 |
| MEAN WTS | PHN82 | 111 | 99 | 91 | 102 | 100 | 101 | 95 | 95 | 100 | 100 |
| MEAN WTS | PHV78 | 98 | 98 | 86 | 99 | 103 | 101 | 103 | 103 | 100 | 100 |
| | DIFF. | 12 | 2 | 4 | 3 | 3 | 0 | 7 | 9 | 0 | |

1 - PHN82 HYBRID
2 - PIONEER ® BRAND 3379

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 119 | 105 | 148.2 | 106 | 20.1 | 138.5 | 93.8 | 95.6 | 98.1 | 5.8 |
| | | 2 | 120 | 106 | 151.3 | 107 | 20.8 | 141.8 | 96.0 | 93.6 | 97.3 | 6.7 |
| | | LOCS | 59 | 55 | 273 | 273 | 276 | 70 | 256 | 128 | 113 | 180 |
| | | DIFF | 1 | 1 | 3.1 | 1 | 0.7 | 3.3 | 2.1 | 1.9 | 0.8 | 0.9 |
| | | PROB | .000# | .380 | .002# | .349 | .000# | .000# | .000# | .002# | .089* | .000# |

| YEAR | REGION | VAR # | TST WTA ABS | COB SC ABS | GRN QUL ABS | SDG VGR ABS | EST CNT ABS | STK CNT ABS | PLT HT ABS | EAR HT ABS | DRP EAR ABS | BRT STK ABS |
|---|---|---|---|---|---|---|---|---|---|---|---|---|
| TOTAL SUM | | 1 | 57.4 | 4.9 | 6.9 | 5.6 | 63.2 | 48.1 | 105.0 | 44.4 | 99.6 | 96.1 |
| | | 2 | 58.0 | 6.2 | 7.2 | 5.8 | 65.5 | 48.4 | 108.0 | 46.4 | 99.5 | 95.4 |
| | | LOCS | 274 | 26 | 93 | 144 | 191 | 291 | 151 | 149 | 195 | 57 |
| | | DIFF | 0.5 | 1.3 | 0.3 | 0.2 | 2.2 | 0.3 | 2.9 | 2.0 | 0.1 | 0.7 |
| | | PROB | .000# | .000# | .001# | .057* | .000# | .063* | .000# | .000# | .277 | .375 |

\* = 10% SIG
+ = 5% SIG
# = 1% SIG

Research Comparisons For Hybrids Having PHN82 As A Parent

Additional comparisons of the characteristics for the hybrid noted above, which has PHN82 as a female parent, were made against Pioneer® brand hybrids 3343 and 3377. These results are shown in Tables 6–7. Pioneer® brand hybrid 3343 is a newer commercial hybrid that is of significant importance in the central and western regions. Pioneer® brand hybrid 3377 is an older hybrid that has been marketed for a number of years in the central and western areas. Hybrids 3379 (shown above), 3343 and the hybrid having PHN82 as a parent are expected to replace 3377 in the central and western Corn Belt areas.

The results in Table 6 show that the PHN82 hybrid is also earlier maturing than Pioneer® brand hybrid 3343. The PHN82 hybrid had fewer barren plants than 3343, better stay green, better grain test weight, had more resistance to ear droppage and is a much shorter plant with a lower ear height than 3343. The results in Table 7 show that the PHN82 hybrid matures earlier than 3377, has approximately the same yield but has a significantly better stalk lodging and root lodging resistance, better barren resistance, better stay green, and much better brittle stalk resistance than 3377. It is a shorter hybrid with lower ear height. The results given in Table 8 and 9 compare the PHN82 hybrid to DeKalb hybrid DK636 and Wyffels hybrid W670. These are commercial hybrids that are representative of the competitive hybrids sold in the same area as the PHN82 hybrid. The results in Table 8 show that the PHN82 hybrid matures earlier than DK636 with very similar yield. The PHN82 hybrid also had fewer barren plants, better stay green, better early stand count and was shorter and lower eared than DK636. The results in Table 9 show that the PHN82 hybrid is later flowering and has lower grain moisture than W670. It had a significantly higher yield than W670, fewer barren plants, better stay green, and better seedling vigor. It is a taller hybrid than W670.

Comparisons of the characteristics for another hybrid having PHN82 as a male parent were made against Pioneer® brand hybrids 3467, 3374, and 3379. These results are shown in Tables 10–12.

The results in Table 10 show that the second PHN82 hybrid has the same relative maturity as Pioneer® brand hybrid 3467 but is somewhat later to shed pollen. It has significantly higher yield, better resistance to stalk lodging and root lodging, and better stay green (plant health at physiological maturity). It is also better in adverse germination conditions, showing superior seedling vigor and early stand count than 3467. It is shorter but has higher ears than 3467. The results in Table 11 show that the second PHN82 hybrid is also the same maturity as Pioneer® brand hybrid 3374 and is also later to shed pollen. The PHN82 hybrid was higher yielding than 3374. It was superior to 3374 for seedling vigor, as well as for dropped ears and brittle stalks. It is a much shorter plant with a lower ear height than 3374, which may have contributed to its superior root lodging performance. The results in Table 12 show that the PHN82 hybrid matures earlier than 3379, and has approximately the same yield but is lower in moisture. It has significantly better root lodging resistance, better barren resistance, fewer dropped ears, and better brittle stalk resistance than 3379. It is a shorter hybrid with lower ear height.

Tables 13 and 14 compare the second PHN82 hybrid to DeKalb-Pfizer hybrid DK636 and Wyffels hybrid W670. The results in Table 13 show that the PHN82 hybrid matures earlier than DK636 with very similar yield. The PHN82 hybrid also had fewer barren plants, better stay green, better seedling vigor and higher early stand count than DK636, all suggestive of better plant health and stress tolerance. It was shorter and lower eared than DK636 and had superior root lodging resistance, which can be important under adverse weather conditions. Overall (as shown by selection index) it is a very superior hybrid. The results in Table 14 show that the PHN82 hybrid is earlier flowering and better yielding with lower grain moisture than W670. It is taller and has higher-placed ears than W670, which is quite short, yet had superior stalk lodging and root lodging performance and fewer brittle stalks than W670.

Strip Test Data for PHN82 Hybrids

Comparison data was collected from strip tests that were grown by farmers. Each hybrid was grown in strips of 4, 6, 8, 12, etc. rows in fields depending on the size of the planter used. The data were collected from strip tests that had the hybrids in the same area of a field. The grain was harvested from a measured area and weighed. The moisture percentage was determined to compute yield and bushels per acre was adjusted to 15.5% moisture. The number of comparisons would represent the number of locations or replications where the two hybrids were grown in the same field in close proximity and compared.

Comparison strip testing was clone between the first PHN82 hybrid noted above, having PHN82 as a female parent, and Pioneer®brand hybrids 3379, 3343 and 3377. Strip testing was also done against DeKalb-Pfizer hybrid DK636.

These results are presented in Table 15. The results illustrate that the PHN82 hybrid had a yield advantage over the three Pioneer hybrids which resulted in a better return on the farmers investment based on adjusted gross income. Although the PHN82 hybrid did not outfield DK636 in the 1988 strip test, that data was based on only one comparison. Its advantages for other characteristics over DK636 will make the PHN82 hybrid an important hybrid in the central and western Corn Belt. Also, the more comprehensive research comparisons above show that there is not a significant yield difference between DK636 and the PHN82 hybrid.

Comparison strip testing was also done between the second PHN82 hybrid, having PHN82 as a male parent, and Pioneer® brand hybrids 3379, 3343 and 3377. Strip testing was also done against DeKalb-Pfizer hybrid DK636.

These results are presented in Table 16. The results illustrate that the PHN82 hybrid had a root lodging score that was better than the three Pioneer hybrids. Although the PHN82 hybrid yield results were mixed, its advantages for other characteristics will make the PHN82 o hybrid an important hybrid in the central and western Corn Belt. Also, the more comprehensive research comparisons above show that the PHN82 hybrid generally provides equal or better yield compared to these hybrids.

Comparison of Key Characteristics for PHN82 Hybrids

Characteristics of the hybrid having PHN82 as a female parent are compared to Pioneer® brand hybrids 3379, 3343, 3377 and also DeKalb-Pfizer hybrid DK636, and Wyffels hybrid W670 in Table 17. Characteristics of the hybrid having PHN82 as a male parent are compared to Pioneer® brand hybrids 3467, 3343, 3379 and also DeKalb-Pfizer hybrid DK636, and Wyffels hybrid W670 in Table 18. The ratings given for most of the traits are on a 1–9 basis. In these cases 9 would be outstanding while a 1 would be poor for the given characteristics. These values are based on performance of the given hybrid relative to other Pioneer® commercial and pre-commercial hybrids that are grown in the trials. The traits characterized in Tables 17 and 18 as "H/POP," "L/POP," "D/D," and "D/T," refer to qualitative evaluations of performance in high planting populations, low planting populations, drydown, and drought tolerance, respectively. The other traits evaluated were defined previously and the ratings utilized not only research data but experience that trained corn researchers had in the field as well as sales experience with the hybrids in strip test and the field. These scores reflect the hybrids' relative performance to other hybrids for the characteristics listed. Table 17 shows that the first PHN82 hybrid offers high yield for its maturity, responds very well to high plant density, has good stay green, has outstanding drought tolerance, is short, and has excellent brittle stalk resistance relative to the other hybrids. Table 18 shows that the second PHN82 hybrid also provides high yield for its maturity, good root lodging resistance and short plant height with low ear placement. It is highly superior for seedling vigor and shows good drought tolerance and drydown.

TABLE 6

HYBRID #1 - PHN82 hybrid
HYBRID #2 - 3343

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 119 | 105 | 149.2 | 105 | 19.9 | 137.4 | 93.1 | 94.5 | 98.1 | 5.6 |
| | | 2 | 121 | 104 | 152.9 | 104 | 20.8 | 145.1 | 95.0 | 94.6 | 96.0 | 5.1 |
| | | LOCS | 44 | 40 | 204 | 204 | 208 | 51 | 188 | 94 | 76 | 134 |
| | | DIFF | 2 | 1 | 3.7 | 1 | 0.9 | 7.7 | 1.9 | 0.0 | 2.1 | 0.4 |
| | | PROB | .000# | .707 | .017+ | .626 | .000# | .000# | .002# | .974 | .001# | .038+ |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 57.4 | 5.0 | 6.9 | 5.7 | 62.3 | 105.4 | 44.8 | 99.5 | 96.7 |
| | | 2 | 57.0 | 6.0 | 6.8 | 6.2 | 62.9 | 112.3 | 49.0 | 99.2 | 95.4 |
| | | LOCS | 207 | 20 | 82 | 114 | 147 | 112 | 111 | 139 | 47 |
| | | DIFF | 0.4 | 1.0 | 0.1 | 0.5 | 0.6 | 6.9 | 4.1 | 0.4 | 1.3 |
| | | PROB | .000# | .005# | .449 | .000# | .224 | .000# | .000# | .005# | .115 |

* = 10% SIG
+ = 5% SIG
# = 1% SIG

TABLE 7

HYBRID #1 - PHN82 hybrid
HYBRID #2 - 3377

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 119 | 104 | 153.5 | 104 | 20.0 | 137.3 | 93.6 | 94.8 | 98.5 | 5.8 |
| | | 2 | 120 | 101 | 154.8 | 104 | 20.4 | 141.8 | 90.5 | 90.3 | 97.6 | 4.7 |
| | | LOCS | 48 | 44 | 245 | 245 | 246 | 62 | 225 | 123 | 95 | 162 |
| | | DIFF | 1 | 3 | 1.4 | 1 | 0.3 | 4.5 | 3.1 | 4.5 | 0.9 | 1.1 |
| | | PROB | .027+ | .198 | .280 | .515 | .000# | .000# | .000# | .000# | .060* | .000# |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 57.5 | 5.0 | 6.6 | 5.7 | 63.9 | 107.8 | 46.0 | 99.6 | 96.2 |
| | | 2 | 57.4 | 5.7 | 6.5 | 5.8 | 64.0 | 111.3 | 49.0 | 99.4 | 92.0 |
| | | LOCS | 245 | 26 | 86 | 137 | 178 | 138 | 136 | 168 | 53 |
| | | DIFF | 0.1 | 0.8 | 0.1 | 0.2 | 0.1 | 3.5 | 3.0 | 0.1 | 4.2 |
| | | PROB | .099* | .003# | .460 | .182 | .756 | .000# | .000# | .161 | .002# |

\* = 10% SIG
+ = 5% SIG
# = 1% SIG

TABLE 8

HYBRID #1 - PHN82 hybrid
HYBRID #2 - DK636

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 119 | 106 | 147.4 | 106 | 19.7 | 140.7 | 93.9 | 98.7 | 97.9 |
| | | 2 | 123 | 100 | 146.1 | 101 | 21.4 | 147.1 | 92.6 | 97.1 | 94.3 |
| | | LOCS | 19 | 19 | 83 | 83 | 85 | 22 | 80 | 35 | 30 |
| | | DIFF | 4 | 7 | 1.3 | 4 | 1.7 | 6.3 | 1.4 | 1.7 | 3.6 |
| | | PROB | .000# | .075* | .584 | .041+ | .000# | .000# | .150 | .141 | .033+ |

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|---|
| TOTAL SUM | | 1 | 5.7 | 57.3 | 4.8 | 7.1 | 5.5 | 63.9 | 100.6 | 41.0 | 99.8 | 100.0 |
| | | 2 | 4.5 | 58.2 | 5.9 | 6.9 | 5.2 | 60.3 | 103.2 | 43.3 | 99.7 | 100.0 |
| | | LOCS | 53 | 85 | 5 | 17 | 39 | 58 | 40 | 40 | 53 | 1 |
| | | DIFF | 1.2 | 0.9 | 1.0 | 0.2 | 0.3 | 3.5 | 2.7 | 2.3 | 0.1 | 0.0 |
| | | PROB | .000# | .000# | .301 | .431 | .123 | .000# | .001# | .001# | .133 | |

\* = 10% SIG
+ = 5% SIG
# = 1% SIG

TABLE 9

HYBRID #1 - PHN82 hybrid
HYBRID #2 - WYF670

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 119 | 107 | 142.8 | 108 | 20.3 | 140.3 | 95.8 | 99.2 | 97.6 |
| | | 2 | 122 | 93 | 130.1 | 97 | 21.4 | 136.8 | 94.6 | 99.2 | 95.6 |
| | | LOCS | 12 | 12 | 51 | 51 | 51 | 14 | 47 | 22 | 20 |
| | | DIFF | 3 | 14 | 12.6 | 11 | 1.1 | 3.5 | 1.1 | 0.0 | 2.0 |
| | | PROB | .000# | .000# | .000# | .000# | .000# | .000# | .143 | .974 | .082* |

TABLE 9-continued

HYBRID #1 - PHN82 hybrid
HYBRID #2 - WYF670

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS |
|---|---|---|---|---|---|---|---|---|---|---|---|
| TOTAL SUM | | 1 | 6.1 | 56.9 | 4.7 | 6.8 | 5.9 | 63.4 | 102.2 | 42.5 | 99.9 |
| | | 2 | 4.8 | 57.1 | 6.3 | 7.1 | 5.5 | 64.7 | 95.4 | 37.4 | 99.9 |
| | | LOCS | 30 | 51 | 3 | 11 | 24 | 31 | 24 | 24 | 31 |
| | | DIFF | 1.3 | 0.2 | 1.6 | 0.3 | 0.4 | 1.3 | 6.8 | 5.1 | 0.0 |
| | | PROB | .000# | .144 | .015+ | .402 | .096* | .070* | .000# | .000# | .983 |

\* = 10% SIG
+ = 5% SIG
# = 1% SIG

TABLE 10

VARIETY #1 - PHN82 hybrid
VARIETY #2 - 3467

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 118 | 106 | 140.5 | 103 | 18.4 | 135.6 | 95.6 | 97.2 | 97.7 | 4.7 |
| | | 2 | 117 | 96 | 133.4 | 99 | 18.3 | 131.3 | 93.1 | 93.6 | 96.8 | 4.3 |
| | | LOCS | 30 | 32 | 123 | 123 | 126 | 42 | 103 | 67 | 38 | 63 |
| | | DIFF | 0 | 9 | 7.2 | 5 | 0.1 | 4.3 | 2.5 | 3.5 | 0.9 | 0.5 |
| | | PROB | .222 | .000# | .000# | .000# | .315 | .000# | .001# | .003# | .108 | .077* |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 58.0 | 5.6 | 7.0 | 5.5 | 61.6 | 106.4 | 44.5 | 99.6 | 99.4 |
| | | 2 | 58.7 | 4.2 | 6.8 | 4.9 | 55.7 | 109.1 | 43.5 | 99.6 | 97.4 |
| | | LOCS | 122 | 9 | 43 | 61 | 72 | 57 | 57 | 80 | 15 |
| | | DIFF | 0.7 | 1.4 | 0.1 | 0.6 | 5.9 | 2.7 | 1.0 | 0.0 | 2.0 |
| | | PROB | .000# | .014+ | .581 | .001# | .000# | .000# | .007# | .756 | .037+ |

\* = 10% SIG
+ = 5% SIG
# = 1% SIG

TABLE 11

VARIETY #1 - PHN82 hybrid
VARIETY #2 - 3374

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 118 | 103 | 139.6 | 102 | 19.2 | 138.7 | 93.9 | 98.2 | 96.7 | 5.0 |
| | | 2 | 118 | 101 | 137.0 | 100 | 18.9 | 136.6 | 95.0 | 97.0 | 94.6 | 4.6 |
| | | LOCS | 25 | 27 | 116 | 116 | 125 | 36 | 100 | 59 | 34 | 57 |
| | | DIFF | 0 | 2 | 2.6 | 3 | 0.2 | 2.2 | 1.1 | 1.2 | 2.1 | 0.4 |
| | | PROB | .146 | .386 | .095* | .056* | .062* | .000# | .139 | .023+ | .017 | .166 |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 57.5 | 6.3 | 6.9 | 5.8 | 60.5 | 100.7 | 42.5 | 99.7 | 98.1 |
| | | 2 | 57.7 | 6.8 | 6.7 | 5.4 | 60.0 | 107.1 | 46.3 | 99.4 | 94.9 |
| | | LOCS | 117 | 11 | 77 | 67 | 94 | 48 | 48 | 64 | 13 |
| | | DIFF | 0.2 | 0.6 | 0.2 | 0.4 | 0.5 | 6.4 | 3.8 | 0.3 | 3.2 |

TABLE 11-continued

VARIETY #1 - PHN82 hybrid
VARIETY #2 - 3374

| | PROB | .089* | .034+ | .159 | .011+ | .157 | .000# | .000# | .014+ | .043+ |

\* = 10% SIG
+ = 5% SIG
# = 1% SIG

TABLE 12

VARIETY #1 - PHN82 hybrid
VARIETY #2 - 3379

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 118 | 103 | 142.6 | 102 | 19.0 | 137.5 | 94.4 | 97.7 | 97.0 | 4.9 |
| | | 2 | 120 | 104 | 143.9 | 103 | 19.5 | 137.3 | 94.6 | 90.9 | 95.5 | 6.1 |
| | | LOCS | 55 | 60 | 239 | 239 | 249 | 73 | 207 | 108 | 66 | 135 |
| | | DIFF | 1 | 1 | 1.3 | 1 | 0.5 | 0.2 | 0.2 | 6.8 | 1.5 | 1.2 |
| | | PROB | .000# | .215 | .160 | .160 | .000# | .608 | .744 | .000# | .074* | .000# |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 57.6 | 6.3 | 7.0 | 5.7 | 60.9 | 104.3 | 43.5 | 99.8 | 98.7 |
| | | 2 | 57.6 | 6.5 | 7.3 | 5.8 | 61.5 | 107.6 | 46.1 | 99.5 | 96.2 |
| | | LOCS | 240 | 15 | 109 | 139 | 171 | 113 | 113 | 133 | 28 |
| | | DIFF | 0.0 | 0.2 | 0.2 | 0.1 | 0.6 | 3.3 | 2.7 | 0.3 | 2.5 |
| | | PROB | .729 | .550 | .028+ | .165 | .062* | .000# | .000# | .005# | .026+ |

\* = 10% SIG
+ = 5% SIG
# = 1% SIG

TABLE 13

VARIETY #1 - PHN82 hybrid
VARIETY #2 - DK636

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 118 | 102 | 141.9 | 101 | 19.0 | 138.0 | 93.5 | 97.1 | 97.4 |
| | | 2 | 123 | 95 | 139.5 | 99 | 20.7 | 138.2 | 91.4 | 89.1 | 95.0 |
| | | LOCS | 34 | 37 | 150 | 150 | 156 | 45 | 134 | 63 | 41 |
| | | DIFF | 5 | 7 | 2.4 | 2 | 1.8 | 0.2 | 2.1 | 8.1 | 2.4 |
| | | PROB | .000# | .004# | .181 | .122 | .000# | .704 | .002# | .000# | .012+ |

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|---|
| TOTAL SUM | | 1 | 4.7 | 57.6 | 6.7 | 7.1 | 5.9 | 60.7 | 102.0 | 42.4 | 99.7 | 99.8 |
| | | 2 | 4.4 | 58.1 | 5.7 | 7.1 | 5.3 | 57.9 | 106.6 | 45.4 | 99.6 | 99.0 |
| | | LOCS | 88 | 152 | 9 | 77 | 88 | 118 | 72 | 72 | 91 | 16 |
| | | DIFF | 0.4 | 0.4 | 1.0 | 0.0 | 0.6 | 2.8 | 4.6 | 3.0 | 0.1 | 0.8 |
| | | PROB | .027+ | .000# | .120 | .831 | .000# | .000# | .000# | .000# | .162 | .104 |

\* = 10% SIG
+ = 5% SIG
# = 1% SIG

TABLE 14

VARIETY #1 - PHN82 hybrid
VARIETY #2 - W670

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 117 | 103 | 133.0 | 102 | 19.1 | 137.1 | 93.9 | 98.2 | 96.7 |
| | | 2 | 122 | 92 | 125.5 | 96 | 20.5 | 130.6 | 91.4 | 96.1 | 96.4 |
| | | LOCS | 25 | 27 | 111 | 111 | 116 | 35 | 96 | 59 | 33 |
| | | DIFF | 4 | 10 | 7.4 | 6 | 1.4 | 6.5 | 2.5 | 2.1 | 0.2 |
| | | PROB | .000# | .000# | .000# | .000# | .000# | .000# | .001# | .003# | .814 |

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|---|
| TOTAL SUM | | 1 | 4.8 | 57.5 | 6.3 | 6.6 | 5.7 | 60.6 | 102.0 | 44.0 | 99.7 | 99.7 |
| | | 2 | 4.4 | 57.6 | 5.6 | 6.4 | 5.8 | 61.1 | 96.0 | 40.0 | 99.7 | 99.0 |
| | | LOCS | 53 | 110 | 9 | 62 | 62 | 80 | 49 | 49 | 79 | 8 |
| | | DIFF | 0.3 | 0.1 | 0.7 | 0.2 | 0.1 | 0.5 | 6.0 | 4.0 | 0.0 | 0.8 |
| | | PROB | .157 | .444 | .063* | .239 | .638 | .174 | .000# | .000# | .886 | .081* |

* = 10% SIG
+ = 5% SIG
# = 1% SIG

TABLE 15

| Brand | Product | Yield | Yld Adv | Wins (%) | Moist | Moist Adv | Wins (%) | Income/Acre | Inc Adv | Wins (%) | Pop K/Acre | Stand (%) | Roots (%) | Tst Wt |
|---|---|---|---|---|---|---|---|---|---|---|---|---|---|---|
| PIONEER | PHN82 hyb | 135.0 | 1.6 | 55 | 19.2 | 1.0 | 70 | 360.77 | 7.28 | 59 | 22.6 | 95 | 97 | 56.4 |
| PIONEER | 3379 | 133.4 | | | 20.2 | | | 353.49 | | | 22.8 | 96 | 96 | 56.6 |
| COMPARISONS | | 263 | | | 263 | | | 263 | | | 191 | 182 | 179 | 243 |
| PIONEER | PHN82 hyb | 129.2 | 8.9 | 66 | 18.8 | 1.3 | 63 | 346.36 | 25.98 | 67 | 22.6 | 95 | 97 | 56.4 |
| PIONEER | 3343 | 120.3 | | | 20.1 | | | 320.38 | | | 22.2 | 93 | 96 | 55.9 |
| COMPARISONS | | 168 | | | 168 | | | 168 | | | 120 | 115 | 113 | 151 |
| PIONEER | PHN82 hyb | 134.7 | 4.6 | 64 | 18.7 | -0.1 | 47 | 361.27 | 12.57 | 62 | 22.4 | 95 | 98 | 56.6 |
| PIONEER | 3377 | 130.1 | | | 18.6 | | | 348.70 | | | 22.2 | 89 | 96 | 56.1 |
| COMPARISONS | | 248 | | | 248 | | | 248 | | | 178 | 170 | 168 | 231 |
| PIONEER | PHN 82 hyb | 74.5 | -23.7 | 0 | 17.2 | 2.0 | 100 | 202.34 | -60.44 | 0 | 0.0 | 0 | 0 | 57.5 |
| DEKALB-PFTZER | DK636 | 98.2 | | | 19.2 | | | 262.78 | | | 0.0 | 0 | 0 | 58.5 |
| COMPARISONS | | 1 | | | 1 | | | 1 | | | 0 | 0 | 0 | 1 |

TABLE 16

Strip test comparison results

| Brand | Product | Yield | Moist | Income/Acre | Pop K/Acre | Stand (%) | Roots (%) | Test Wt |
|---|---|---|---|---|---|---|---|---|
| PIONEER | PHN82 | 157.8 | 19.0 | 343.09 | 23.8 | 93 | 97 | 57.5 |
| WEIGHTED AVG | | 158.5 | 18.8 | 345.34 | 23.5 | 91 | 94 | 57.4 |
| Advantage | | -0.7 | -0.2 | -2.25 | 0.3 | 2 | 3 | 0.1 |
| Number of Comparisons | | 528 | 528 | 528 | 284 | 225 | 209 | 340 |
| Percent Wins | | 45 | 41 | 45 | 46 | 43 | 20 | 40 |
| Probability of Difference | | 86 | 99 | 96 | 96 | 99 | 99 | 81 |
| PIONEER | PHN82 | 159.9 | 19.9 | 345.63 | 23.7 | 94 | 98 | 57.4 |
| PIONEER | 3374 | 157.4 | 19.2 | 342.24 | 24.6 | 92 | 94 | 57.6 |
| Advantage | | 2.5 | -0.7 | 3.39 | -0.9 | 2 | 4 | -0.2 |
| Number of Comparisons | | 84 | 84 | 84 | 27 | 21 | 20 | 29 |
| Percent Wins | | 61 | 30 | 58 | 33 | 47 | 25 | 20 |
| Probability of Difference | | 97 | 99 | 80 | 93 | 63 | 90 | 61 |

TABLE 16-continued

Strip test comparison results

| Brand | Product | Yield | Moist | Income/ Acre | Pop K/Acre | Stand (%) | Roots (%) | Test Wt |
|---|---|---|---|---|---|---|---|---|
| PIONEER | PHN82 | 158.3 | 18.7 | 345.04 | 24.2 | 94 | 97 | 57.8 |
| PIONEER | 3379 | 158.1 | 18.6 | 344.96 | 23.6 | 91 | 93 | 57.5 |
| Advantage | | 0.2 | −0.1 | 0.08 | 0.6 | 3 | 4 | 0.3 |
| Number of Comparisons | | 195 | 195 | 195 | 108 | 86 | 78 | 134 |
| Percent Wins | | 48 | 37 | 49 | 49 | 39 | 23 | 44 |
| Probability of Difference | | 17 | 78 | 4 | 98 | 92 | 99 | 99 |
| PIONEER | PHN82 | 155.8 | 18.6 | 339.96 | 23.4 | 93 | 96 | 57.3 |
| PIONEER | 3467 | 154.3 | 18.2 | 337.82 | 22.0 | 90 | 92 | 58.0 |
| Advantage | | 1.5 | −0.4 | 2.14 | 1.4 | 3 | 4 | −0.7 |
| Number of Comparisons | | 75 | 75 | 75 | 58 | 47 | 44 | 72 |
| Percent Wins | | 54 | 44 | 50 | 67 | 48 | 22 | 18 |
| Probability of Difference | | 72 | 93 | 50 | 99 | 92 | 90 | 99 |
| PIONEER | PHN82 | 170.6 | 17.5 | 376.41 | 0.0 | 0 | 0 | 61.0 |
| DEKALB | DK636 | 155.0 | 19.6 | 336.74 | 0.0 | 0 | 0 | 60.0 |
| Advantage | | 15.6 | 2.1 | 39.67 | 0.0 | 0 | 0 | 1.0 |
| Number of Comparisons | | 2 | 2 | 2 | 0 | 0 | 0 | 1 |
| Percent Wins | | 50 | 100 | 50 | 0 | 0 | 0 | 100 |
| Probability of Difference | | 30 | 53 | 36 | 0 | 0 | 0 | 0 |
| PIONEER | PHN82 | 158.6 | 19.1 | 345.22 | 26.3 | 82 | 84 | 0.0 |
| WYFFELS | W670 | 154.5 | 20.0 | 334.12 | 26.9 | 68 | 84 | 0.0 |
| Advantage | | 4.1 | 0.9 | 11.10 | −0.6 | 14 | 0 | 0.0 |
| Number of Comparisons | | 10 | 10 | 10 | 4 | 2 | 2 | 0 |
| Percent Wins | | 70 | 60 | 70 | 25 | 50 | 0 | 0 |
| Probability of Difference | | 56 | 82 | 66 | 23 | 50 | 0 | 0 |

TABLE 17

| HYBRID | MST RM | GDU BL | GDU SLK | YLD | H/POP | L/POP | D/D | S/L | R/L | STGR | D/T |
|---|---|---|---|---|---|---|---|---|---|---|---|
| PHN82 | 119 | 2777 | 1460 | 9 | 9 | 5 | 5 | 5 | 5 | 7 | 9 |
| 3379 | 119 | 2873 | 1483 | 9 | 9 | 6 | 8 | 7 | 5 | 9 | 8 |
| 3343 | 121 | 2803 | 1503 | 8 | 6 | 8 | 5 | 6 | 6 | 6 | 4 |
| W670 | 121 | 2715 | 1427 | 6 | 7 | 4 | 3 | 5 | 6 | 5 | 6 |
| 3377 | 122 | 2791 | 1462 | 7 | 5 | 8 | 6 | 2 | 3 | 3 | 7 |
| DK636 | 123 | 2768 | 1454 | 7 | 7 | 8 | 4 | 4 | 6 | 3 | 7 |

| HYBRID | T/WT | COB | QUAL. | P/SDG | S/VIG | ESC | P/HT | E/HT | D/E | B/STK |
|---|---|---|---|---|---|---|---|---|---|---|
| PHN82 | 4 | 3 | 5 | 3 | 5 | 5 | 3 | 3 | 5 | 8 |
| 3379 | 5 | 5 | 5 | 3 | 4 | 5 | 4 | 4 | 5 | 8 |
| 3343 | 4 | 5 | 3 | 7 | 7 | 7 | 7 | 7 | 4 | 5 |
| W670 | 4 | 6 | 4 | — | 5 | 6 | 2 | 1 | 4 | — |
| 3377 | 4 | 4 | 5 | 6 | 5 | 5 | 5 | 5 | 7 | 3 |
| DK636 | 6 | 5 | 8 | — | 4 | 4 | 4 | 4 | 6 | 8 |

TABLE 18

HYBRID PATENT COMPARISONS - CHARACTERISTICS

| HYBRID | GDU SLK | GDU BL | MST RM | YLD | H/POP | L/POP | D/D | S/L | R/L |
|---|---|---|---|---|---|---|---|---|---|
| PHN82 | 1491 | 2800 | 118 | 8 | 8 | 5 | 8 | 6 | 7 |
| 3467 | 1447 | 2741 | 116 | 7 | 6 | 6 | 6 | 4 | 6 |
| 3374 | 1460 | 2823 | 118 | 8 | 6 | 8 | 9 | 7 | 8 |
| 3379 | 1477 | 2858 | 119 | 8 | 9 | 6 | 9 | 7 | 5 |
| W670 | 1405 | 2723 | 122 | 8 | 9 | 5 | 3 | 5 | 7 |
| DK636 | 1474 | 2760 | 123 | 7 | 7 | 6 | 4 | 4 | 6 |

| HYBRID | STGR | D/T | T/WT | QUAL. | S/VIG | P/HT | E/HT | D/E | B/STK |
|---|---|---|---|---|---|---|---|---|---|
| PHN82 | 5 | 8 | 5 | 5 | 7 | 3 | 3 | 5 | 6 |
| 3467 | 4 | 7 | 6 | 5 | 3 | 5 | 3 | 6 | 5 |

TABLE 18-continued

| HYBRID PATENT COMPARISONS - CHARACTERISTICS | | | | | | | | |
|---|---|---|---|---|---|---|---|---|
| 3374 | 5 | 6 | 5 | 5 | 5 | 6 | 5 | 5 | 3 |
| 3379 | 9 | 8 | 5 | 5 | 4 | 4 | 4 | 5 | 8 |
| W670 | 5 | 9 | 5 | 4 | 5 | 2 | 1 | 6 | 8 |
| DK636 | 3 | 7 | 6 | 8 | 4 | 4 | 4 | 6 | 8 |

Deposits

A deposit of the inbred seed of this invention is maintained by Pioneer Hi-Bred International, Inc., 700 Capital Square, 400 Locust Street, Des Moines, Iowa 50309. Access to this deposit will be available during the pendency of this application to persons determined by the Commissioner of Patents and Trademarks to be entitled theretounder 37 CFR 1.14 and 35 USC 122. Upon allowance of any claims in this application, all restrictions on access required to be removed will be removed by affording access to a deposit of the same inbred seed with the American Type Culture Collection, Rockville, Md., ATCC Accession No. 75254.

What is claimed is:

1. A process for producing a hybrid corn seed which gives rise to a hybrid corn plant having alleles which, when expressed, contribute to hybrids which are stress tolerant coupled with good yield when compared to similar maturity hybrids, possess superior seedling vigor, drought tolerance, low level of brittlesnap and resistance to root and/or stalk lodging, comprising the steps of:

(a) planting, in pollinating proximity, seed of corn inbred line PHN82 having ATCC Accession No. 75254 and another inbred line that is not PHN82;
   (b) cultivating corn plants resulting from said planting until the plants bear flowers;
   (c) inactivating the male reproductive system prior to pollination of the plants of the female inbred line;
   (d) allowing natural cross pollinating to occur between the inbred lines; and
   (e) harvesting seeds produced on said inactivated plants of the inbred line.

2. $F_1$ hybrid corn seed and plants grown therefrom produced by crossing inbred corn plant PHN82 having ATCC No. 75254 with another, different corn plant that is not PHN82 and plants and parts thereof produced from the $F_1$ hybrid seed.

3. A tissue culture initiated from the cells of the corn plant according to claim 2.

* * * * *